United States Patent [19]
Wood et al.

[11] Patent Number: 4,959,265
[45] Date of Patent: Sep. 25, 1990

[54] PRESSURE-SENSITIVE ADHESIVE TAPE FASTENER FOR RELEASABLY ATTACHING AN OBJECT TO A FABRIC

[75] Inventors: Leigh E. Wood, Woodbury; Allen L. Noreen, Lake Elmo, both of Minn.

[73] Assignee: Minnesota Mining and Manufacturing Company, St. Paul, Minn.

[21] Appl. No.: 338,324

[22] Filed: Apr. 17, 1989

[51] Int. Cl.⁵ .................. A61F 13/16; C09U 7/02; B32B 3/06
[52] U.S. Cl. .................. 428/343; 428/100; 604/387; 604/388; 604/389
[58] Field of Search .............. 428/343, 100; 604/389, 604/387, 388; 24/31 V

[56] References Cited

U.S. PATENT DOCUMENTS

| | | | |
|---|---|---|---|
| 4,181,752 | 1/1980 | Martens et al. | 427/54.1 |
| 4,303,485 | 12/1981 | Levens | 204/159.24 |
| 4,336,804 | 6/1982 | Roeder | 604/387 |
| 4,337,772 | 7/1982 | Roeder | 128/290 R |
| 4,376,440 | 3/1983 | Whitehead et al. | 604/387 |
| 4,397,905 | 8/1983 | Dettmer et al. | 428/180 |
| 4,576,850 | 3/1986 | Martens | 428/156 |
| 4,578,069 | 3/1986 | Whitehead et al. | 604/389 X |
| 4,699,622 | 10/1987 | Toussant et al. | 604/389 |
| 4,743,242 | 5/1988 | Grube et al. | 604/389 |

Primary Examiner—George F. Lesmes
Assistant Examiner—D. R. Zirker
Attorney, Agent, or Firm—Donald M. Sell; Roger R. Tamte; William J. Bond

[57] ABSTRACT

An article can be releasably attached to a fabric or other foraminous substrate by means of a pressure-sensitive adhesive tape fastener, the backing of which has an array of bluntly pointed stems protruding beyond the pressure-sensitive adhesive. The back face of the fastener can have an adhesive layer by which it can be adhered to a sanitary napkin, and the napkin can be releasably attached to an undergarment by allowing the stems to penetrate into openings in the fabric of the undergarment until the pressure-sensitive adhesive becomes releasably bonded to the fabric. The fastener can be more supple and less obtrusive than are "Velcro" fasteners and can be produced at significantly lower cost.

13 Claims, 1 Drawing Sheet

PRESSURE-SENSITIVE ADHESIVE TAPE FASTENER FOR RELEASABLY ATTACHING AN OBJECT TO A FABRIC

BACKGROUND OF THE INVENTION

1. Field of the Invention

The invention concerns a pressure-sensitive adhesive tape fastener by which an article can be releasably attached to a fabric or other foraminous substrate, e.g., a sanitary napkin to an undergarment.

2. Description of the Related Art

"Velcro" hook-and-loop-fasteners are widely used for releasably fastening articles to fabrics, but this requires one element of the "Velcro" fastener to be secured to the article and the other to be secured to the fabric. For some uses, it is desirable to secure a fastening element only to the article and not to the fabric. For example, in U.S. Pat. No. 4,376,440 (Whitehead et al.), the underside of a sanitary napkin and other disposable absorbent pads is provided with means for releasably fastening it to an ordinary undergarment. The fluid impervious baffle of the napkin has recessed areas containing pressure-sensitive adhesive that, when exposed, releasably adheres the napkin to an undergarment. Three embodiments are illustrated. In that of FIG. 1, the baffle is an open-cell foam, and the pressure-sensitive adhesive is located within cells of the foam and is exposed by compressing the foam. In FIG. 2, the baffle is a mat of fibers, and in FIG. 3, the baffle is a polypropylene or polyethylene film made with dimpled indentations for the pressure-sensitive adhesive.

In U.S. Pat. No. 4,337,772 (Roeder), the baffle of a sanitary napkin has a pattern of pressure-sensitive adhesive strips which are separated by nonpressure-sensitive adhesive strips that are from 2 to 10 times greater in thickness than the pressure-sensitive adhesive strips. The nonpressure-sensitive adhesive strips permit the napkin to be marketed without a release liner but permit the pressure-sensitive adhesive strips to releasably adhere the napkin to an undergarment.

OTHER PRIOR ART

U.S. Pat. No. 4,397,905 (Dettmer et al.) shows in FIG. 2 a pressure-sensitive adhesive tape, the backing of which is a thermoplastic film that is embossed to have groove-like impressions on the adhesive face and bead-like protrusions on the back face that permit the tape to be unwound from roll form even though it has no antiadhesive coating on the back face.

SUMMARY OF THE INVENTION

The invention provides a pressure-sensitive adhesive tape fastener by which an article can be releasably attached to a fabric or other foraminous substrate. While that objective is accomplished in the Whitehead and Roeder patents when the article is a sanitary napkin, the fastener of the invention is useful for releasably attaching any of a wide variety of articles to foraminous substrates and should provide more reliable fastening even in the specific use to which those patents are directed.

Briefly, the pressure-sensitive adhesive tape fastener of the invention includes (a) a backing having an array of upstanding stemlike projections distributed across at least one face, and (b) a pressure-sensitive adhesive filling the spaces between the projections to an average depth less than the average height of the projections.

The stemlike projections (here sometimes called "stems") should be resistant to compression and bending, and their tips preferably are substantially pointed to permit them to penetrate easily into interstices of a foraminous substrate, even though they may be quite supple. Preferably the points are blunt to avoid any cutting action. For most uses, each of the stems should be less than 2 mm in breadth at the average plane of the surface of the adhesive.

The backing with its stems preferably is formed from a tough thermoplastic resin by cast molding or extrusion molding. Substantially any thermoplastic material suitable for film production can be used to produce the backing. Preferred thermoplastic resins include polyethylene, polypropylene, polyester, and nylon, each of which affords a resilience and flexibility that is helpful for most uses. Also of utility are copolymers of ethylene and propylene and copolymers of ethylene and vinyl acetate.

The thickness of the backing in areas between the stems preferably is from 25 to 500 $\mu$m. If that thickness were substantially less than 25 $\mu$m, the backing might break in use. When that thickness is about 250 $\mu$m or less, the pressure-sensitive adhesive tape fastener of the invention can be more supple and less obtrusive than are "Velcro" fasteners and can be produced at significantly lower cost.

Each of the stems preferably is substantially conical or pyramidal. Such stems can be given mushroom shape by softening the tip of each to create a bulbous crown. A mushroom-shaped stem can mechanically enhance the attachment of the novel pressure-sensitive adhesive tape fastener to a foraminous substrate, as can projections that have hooked crowns. Also useful are cylindrical and rectangular stems. Regardless of the shape of the stems, their tips preferably are shaped to enhance penetration into a fabric or other foraminous substrate.

The pressure-sensitive adhesive may be coated over the stems from solution or emulsion or may be applied by coating a composition that can be polymerized in situ to a pressure-sensitive adhesive state, e.g., by exposure to ultraviolet radiation. The resulting dried or polymerized pressure-sensitive adhesive preferably is at least 25 $\mu$m in depth in order to afford reasonably strong bonding to closely woven fabrics and preferably is at least 100 $\mu$m in depth when the substrate is more coarse such as a carpet backing. Adhesive thicknesses substantially greater than 200 $\mu$m would usually be wasteful of raw material.

The height to which the crowns of the stems should extend above the pressure-sensitive adhesive depends both upon the spacing between stems and upon the coarseness of the fabric or other foraminous substrate to which the novel fastener is to be attached. For attachment to very fine fabrics, it can be sufficient for the stems to protrude only about 20 to 200 $\mu$m beyond the average plane of the surface of the pressure-sensitive adhesive. With such short stems, the novel fastener can have a pleasant feel like that of a matte finish. For attachment to coarse materials such as a heavy jute carpet backing, the stems can protrude from 0.5 to 3.0 mm or more beyond the average plane of the adhesive surface.

In order to hold their shape and penetrate easily into the openings of a foraminous substrate, the stems preferably are of substantially uniform height that exceeds their breadth at the base. They preferably are substantially uniformly spaced, and that spacing preferably is sufficiently large that when the novel fastener is pressed against a substrate and the tips of its stems penetrate the substrate, a relatively large area of pressure-sensitive adhesive comes into contact with the substrate. To do this, the area of the surface of the pressure-sensitive adhesive preferably exceeds the area occupied by the stems in the average plane of the adhesive surface. For most uses, the area of the adhesive surface is from 3 to 30 times that of the stems in said plane.

Instead of being used to attach an article to a foraminous substrate, two pieces of the novel fastener can each be secured to an article and used to releasably attach those two articles to each other. In doing so, the stems of each piece penetrate into the pressure-sensitive adhesive between the stems of the other piece. For example, one piece can be secured to the face of an ear of the front panel of a diaper and a second piece can be secured to the underside of the adjacent ear of the back panel of the diaper. The bond between the two pieces can be of various strengths depending upon the nature of the pressure-sensitive adhesive.

When the back face of the novel fastener is smooth and flat, that face can bear an adhesive layer, e.g., a pressure-sensitive adhesive layer. When the fastener is wound upon itself in roll form for convenience in storage and shipment, a pressure-sensitive adhesive layer on the back face is contacted only by the tips of the stems when the thickness of the coating is less than the height to which the stems protrude above the surface of the adhesive on the face of the fastener. Because the tips of the stems typically are blunt points, the low area of contact provides easy unwinding without any low-adhesion treatment of the tips.

DETAILED DESCRIPTION OF THE INVENTION

Figure 1:
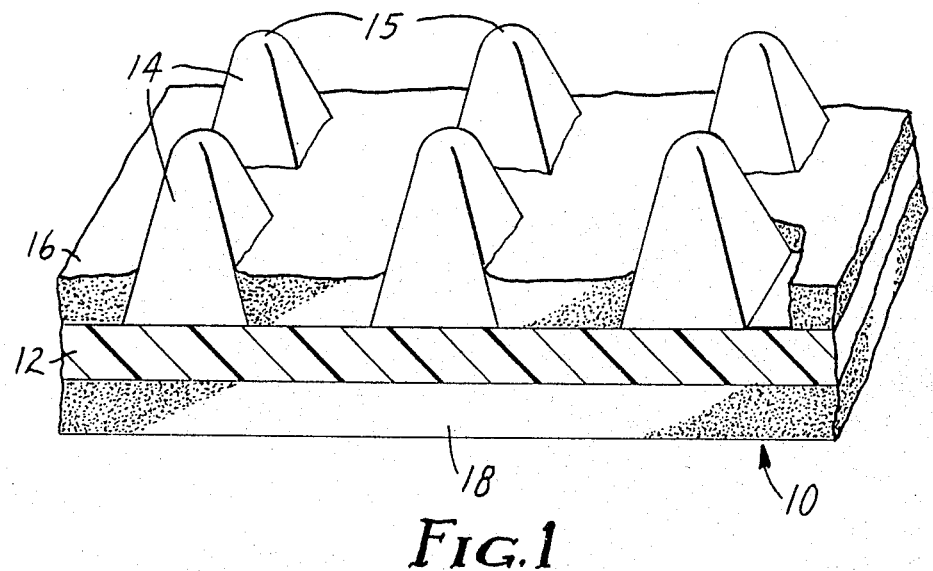

When the back face of a piece of the novel fastener is flat, it can readily be adhesively bonded to a surface of an article which the novel fastener is to attach to a substrate. For example, a novel fastener can be adhesively bonded to the baffle of a sanitary napkin or absorbent pad to permit the napkin to be releasably attached to an undergarment. In another use, a novel fastener can be adhesively bonded to the face of an ear of the front panel of a disposable diaper to permit the fastener to become releasably attached to the nonwoven fabric on the underside of the adjacent ear of the back panel of the diaper.

The pressure-sensitive adhesive that fills the spaces between the stems should be selected to afford good adhesion to the fabric or other foraminous substrate to which articles are to be releasably attached by the novel fastener. Preferred pressure-sensitive adhesives include natural rubber/resin systems, synthetic rubber/resin systems, and acrylate copolymers. Such pressure-sensitive adhesives are described in Wake: "Adhesion and the Formulation of Adhesives", 2nd Ed., Applied Science Publishers, London (1982). The adhesive is generally coated from solutions and then allowed to dry to a tacky state, but other liquid compositions can be applied and converted to a pressure-sensitive adhesive, e.g., by coating polymerizable liquids as taught in U.S. Pat. 4,181,752 or 4,303,485.

The pressure-sensitive adhesive properties of the novel fasteners can be evaluated by typical tape testing procedures as follows.

90° PEEL ADHESION TEST

The substrate is prepared by attaching a 2.5 inch by 6 inch (6.35 by 15.2 cm) piece at two ends of a steel panel (leaving a 5-inch length free in test area). A one-inch (2.54-cm) strip of a fastener is placed with its stems against a substrate (in the cross direction of the substrate) and rolled down twice under the weight of a 2.0-kg roll. The force required to peel the fastener from the substrate at 90° and at 30 cm/min is measured (while the ends of the substrate are fixed to a steel panel leaving a 5-inch (12.5 cm) length of the substrate free in the test area).

DYNAMIC SHEAR ADHESION TEST

The substrate is prepared by attaching a 2.5 inch by 6 inch (6.35 by 15.2 cm) piece at two ends of a steel panel as in the 90° Peel Adhesion Test (leaving a 5-inch length free in test area). A one-inch (2.54-cm) square piece of a fastener is placed against a substrate and rolled down twice with the weight of a 2.0-kg roller. The fastener is oriented on the substrate so that the shear force is exerted in the direction perpendicular to the machine direction of the substrate. The force required to cause shear adhesion failure o the bond between the fastener and the substrate is measured with a tensile tester (Instron Model 1122) at a crosshead speed of 12.7 cm per minute.

WEIGHTED DYNAMIC SHEAR TEST

A sandwich of a fastener, substrate, and steel panel is prepared as in the 90° Peel Adhesion Test. The panel is placed in a Quick Stick Test Jig as described in Pressure-Sensitive-Adhesive Tape Council, Section 2.11 and a 250-gram weight (2.54 cm by 2.54 cm) is placed on top of the fastener. The force required to cause shear failure of this sandwich is measured with a tensile tester (Instron Model 1122) at a crosshead speed of 12.7 cm per minute.

THE DRAWING

Figure 2:
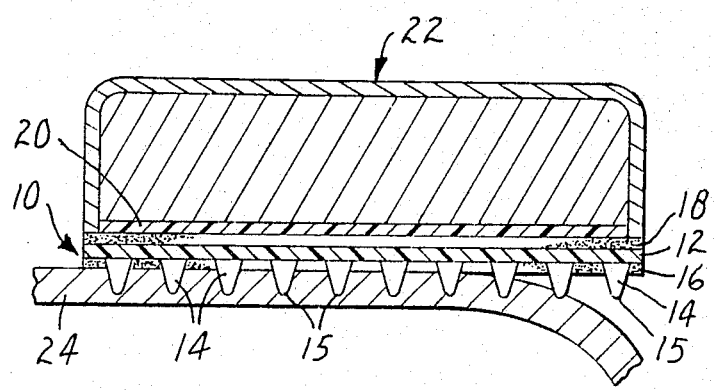

The invention may be more easily understood in reference to the drawing, of which FIG. 1 is a schematic isometric view of a pressure-sensitive adhesive tape fastener of the invention, partly cut away to a vertical cross section; and FIG. 2 shows in cross section the use of the fastener of FIG. 1 for releasably fastening a sanitary napkin to an undergarment.

As shown in FIG. 1, a fastener 10 has a flexible backing 12, from the front face of which project an array of upstanding pyramidal stems or stemlike projections 14, the tips 15 of which are blunt points. In the illustrated embodiment, the stems 14 are uniformly distributed across the front face in straight rows extending in both the lengthwise and crosswise (not shown) directions, though they could be organized in other arrangements, e.g., in staggered rows or not in rows at all. A pressure-sensitive adhesive 16 fills the spaces between the stems to an average depth less than the average height of the stems. As shown in FIG. 1, the surface of the adhesive can vary in height, but there is referred to herein an average plane of the surface of the adhesive which is determined by measuring the total volume of adhesive and dividing that volume by the total area covered by the adhesive. Covering the back face of the fastener 10 is an adhesive layer 18.

As shown in FIG. 2, a piece of the fastener 10 has been adhered by its adhesive layer 18 to the baffle 20 of a sanitary napkin 22. Its pressure-sensitive adhesive 16 has been pressed against the crotch portion 24 of an undergarment by allowing the stems 14 to penetrate into openings in the undergarment fabric.

applied to the forming roll to fill the holes and provide a backing integral with the resulting projections when the quenched resin was stripped off of the forming roll to yield the backing of Example 6. The physical dimensions of the backing of Example 6 are included in Table I.

TABLE I

| Ex | Stem Height ($\mu$m) | Stem Width at Base ($\mu$m) | Stem Spacing* ($\mu$m) | Stems Per $cm^2$ | Projection Shape | Backing thickness** ($\mu$m) | Resin |
|---|---|---|---|---|---|---|---|
| 1 | 76 | 60 | 127 | 6202 | Pyramidal | 450 | A |
| 2 | 381 | 220 | 635 | 236 | Cylindrical | 229 | A |
| 3 | 381 | 220 | 635 | 236 | Cylindrical | 178 | B |
| 4 | 450 | 280 | 1422 | 27 | Conical | 229 | A |
| 5 | 450 | 280 | 2921 | 14 | Conical | 229 | A |
| 6 | 762 | 410 | 1270 | 26 | Pyramidal | 229 | A |

*center to center
**between stems
Resin A - Copolymer of ethylene and propylene from Fina Chemical Co. as resin number 9618.
Resin B - Polyester ("Hytrel" 5556) from E. I. Du Pont.

In the following examples, all parts are given by weight, except as noted:

EXAMPLE 1
(backing)

Two pieces (3 cm by 5 cm) of film (9.5 mil thick prepared by cast extrusion of an ethylene-propylene copolymer resin available as resin number 9618, Fina Oil and Chemical Co., Dallas, Texas) were placed on a metal plate which had the negative impression to produce a stem geometry and pattern as illustrated in FIG. 1 of the drawing. A flat metal plate was placed on top of the film. This was pressed in a platen press at 2500 psi (176 kg/cm), 191° C. for 8 seconds. Then after one minute in cold water, the embossed film was removed. Physical dimensions of the stems are reported in Table I.

EXAMPLES 2-5
(backings)

Examples 2-5 were prepared as in Example 1 with the exception of Example 3 in which the temperature was 240° C. and the pressure was 3000 psi (210 kg/cm). The dimensions of these examples are included in Table I.

EXAMPLE 6
(backing)

Molten resin number 9618, Fina Oil and Chemical Co., Dallas, Texas, was continuously cast onto a rotating steel forming roll using a standard single screw extruder. The forming roll had an array of holes drilled in it representing the negative of a desired projection geometry and spacing. The holes were formed in the forming roll with Minitool microdrilling heads, available from Minitool, Inc., Campbell, CA. To facilitate flow of the molten polymer into the holes the surface of the forming roll was exposed to a vacuum (46.8 mm of mercury) during the casting process using a vacuum chamber preceding and attached to the extrusion die and seated directly on the forming roll. The temperature of the forming roll was maintained at about 35° C. by standard means of internal roll cooling with circulating water.

A gap was provided between the extrusion die and the forming roll to allow sufficient molten resin to be

EXAMPLE 7
(fastener)

A pressure-sensitive adhesive (PSA) was solution coated onto the textured or stem side of the backing by pouring a solution of the adhesive onto the backing. To ensure an even layer, the spreading was aided by the use of a tongue depressor. The pressure-sensitive adhesive was a tackified synthetic rubber, namely an ABA block copolymer of styrene and isoprene, the styrene blocks being the A blocks and comprising about 21% by weight of the total polymer. The composition of this adhesive was 43 parts "Kraton" 1111, a synthetic block copolymer rubber from Shell Chemical Co.; 51 parts "Wingtack Plus", a hydrocarbon tackifying resin from Goodyear Chemical Co.; and 6 parts "Shellflex" 371 oil from Shell Chemical Co. This composition was coated from a 25% solution of a 4:1 mixture of heptane and toluene.

After the pressure-sensitive adhesive solution was spread out onto the backing, it was allowed to air dry at ambient temperature for five minutes and then dried for 20 minutes in a circulating air oven at a temperature of 62° C. The dry weight of the adhesive coat was 38 g/$m^2$. The stem face of the resulting fastener had no detectable tack, e.g., thumb tack, even though no effort had been made to keep the adhesive solution off the tops of the stems. The combined effect of gravity and wetting had resulted in minimal adhesive remaining on the tops, or near the tops, of the stems.

EXAMPLES 8-12
(fasteners)

Examples 8-12 were prepared as was Example 7 using the backings and adhesives indicated in Table II.

TABLE II

| Example | Backing of | PSA Composition | Adhesive Thickness ($\mu$m) |
|---|---|---|---|
| 7 | Example 1 | A | 41 |
| 8 | Example 2 | A | 51 |
| 9 | Example 2 | B | 41 |
| 10 | Example 4 | A | 64 |
| 11 | Example 5 | A | 64 |

TABLE II-continued

| Example | Backing of | PSA Composition | Adhesive Thickness (μm) |
| --- | --- | --- | --- |
| 12 | Example 6 | A | 56 |

PSA A - 43 parts "Kraton" 1111, 51 "Wingtack Plus", and 6 parts "Shellflex" oil #371.
PSA B - 71 parts isooctyl acrylate:acrylic acid copolymer (94.5:5.5), 29 parts "Floral" 85, a rosin based resin from Hercules, Inc., coated from a 25 percent solution of isopropyl alcohol and heptane (7:3).

The fasteners of Examples 7-12 were tested for adhesion to various fabrics and to polyethylene film (0.3 mm) thick as reported in Tables III-V.

TABLE III

90° Peel Adhesion Test
(grams per 2.54 cm width)

| | Substrate | | | | |
| --- | --- | --- | --- | --- | --- |
| Example | Velvet | Cotton | Polyester | Silk | Polyethylene |
| 7 | 150 | 235 | 290 | 425 | 0 |
| 8 | 500 | 300 | 200 | 450 | 0 |
| 9 | 325 | 15 | 2 | 0 | 0 |
| 10 | 280 | 340 | 80 | 30 | 0 |
| 11 | 125 | 180 | 105 | 125 | 0 |
| 12 | 275 | 75 | 50 | 10 | 0 |

TABLE IV

Dynamic Shear Test
(grams per 6.45 square cm)

| | Substrate | | | | |
| --- | --- | --- | --- | --- | --- |
| Example | Velvet | Cotton | Polyester | Silk | Polyethylene |
| 7 | 2500 | 520 | 100 | 100 | <10 |
| 8 | 1000 | 500 | 100 | 10 | <10 |
| 9 | 135 | 190 | 15 | 10 | <10 |
| 10 | 4000 | 2000 | 750 | 650 | <10 |
| 11 | 4000 | 1300 | 700 | 120 | <10 |
| 12 | 2200 | 325 | 360 | 140 | <10 |

TABLE V

Weighted Dynamic Shear Adhesion
(grams per 6.45 square cm)

| | Substrate | | | | |
| --- | --- | --- | --- | --- | --- |
| Example | Velvet | Cotton | Polyester | Silk | Polyethylene |
| 7 | 3000 | 1250 | 1800 | 760 | <10 |
| 8 | 2250 | 1400 | 2800 | 1000 | <10 |
| 9 | >5000 | 1150 | 2400 | 950 | <10 |
| 10 | >5000 | 2800 | 2000 | 1750 | <10 |
| 11 | >5000 | 2250 | 1050 | 950 | <10 |
| 12 | 4250 | 1550 | 4500 | 1250 | <10 |

The backing of the novel fastener can be molded continuously and then continuously coated with pressure-sensitive adhesive. When the backing is flexible, the resulting fastener can be wound upon itself for storage or shipment. Upon being unwound, it can be cut to useful lengths.

Another technique for making the backing of the novel fastener is by replicating a negative molding surface with a resin composition, e.g., a radiation-curable resin composition such as is disclosed in U.S. Pat. No. 4,576,850 (Martens). In order to provide a backing of greater strength, a tough plastic film (e.g., biaxially oriented polypropylene) can be pressed against the resin composition while it is being cured.

In addition to uses mentioned above, the novel fastener can be used for name tags, to provide refastenable envelopes, to attach shoulder pads and underarm pads to garments, to provide a fastening area on an article such that when pressed against another article relative shifting of the articles is limited (see U.S. Pat. No. 4,699,622), and to provide repositionable fastening means for cloth or nonwoven fabrics such as hospital gowns, disposable bed pads, and bandages. In such uses it can be much less-obtrusive than are "Velcro" fasteners. Unlike "Velcro" fasteners which require two elements (hook and loop), the novel fastener is a single element, thus greatly simplifying use and inventories.

What is claimed is:

1. Pressure-sensitive adhesive tape fastener comprising
    (a) a backing having an array of upstanding stems distributed across at least one face, having bases adjacent said at least one face and projecting outwardly from said face to a tip adapted to penetrate a foraminous substrate and wherein the height of the stem is the distance between the base and the outermost point on said tip, and
    (b) a pressure-sensitive adhesive layer on said face partially filling the spaces between the stems where the average adhesive depth is less than the average height of the stems.

2. Pressure-sensitive adhesive tape fastener as defined in claim 1 wherein the backing and stems are formed of a thermoplastic resin.

3. Pressure-sensitive adhesive tape fastener as defined in claim 1 wherein each of the stems has a blunt pointed tip.

4. Pressure-sensitive adhesive tape fastener as defined in claim 3 wherein each of the stems is substantially conical or pyramidal.

5. Pressure-sensitive adhesive tape fastener as defined in claim 3 wherein each of the stems is substantially cylindrical.

6. Pressure-sensitive adhesive tape fastener as defined in claim 1 wherein each of the stems is less than 2 mm in breadth at the average plane of the surface of the pressure-sensitive adhesive layer.

7. Pressure-sensitive adhesive tape fastener as defined in claim 1 wherein the area of the surface of said pressure-sensitive adhesive exceeds the area occupied by the cross sections of the stems in the average plane of the adhesive layer surface.

8. Pressure-sensitive adhesive tape fastener as defined in claim 7 wherein the area of the surface of said adhesive layer is from 3 to 30 times that of the cross sections of the stems in said plane.

9. Pressure-sensitive adhesive tape fastener as defined in claim 1 wherein the backing comprises a thermoplastic film.

10. Pressure-sensitive adhesive tape fastener as defined in claim 1 wherein the average depth of said pressure-sensitive adhesive layer is from 25 to 250 μm.

11. Pressure-sensitive adhesive tape fastener as defined in claim 10 wherein the stems are of substantially uniform height.

12. Pressure-sensitive adhesive tape fastener as defined in claim 11 wherein the stems protrude from 20 to 200 μm beyond the average plane of the surface of the pressure-sensitive adhesive layer for attachment to closely woven fabrics.

13. Pressure-sensitive adhesive tape fastener as defined in claim 11 wherein the stems protrude from 0.5 to 3.0 mm beyond the average plane of the surface of the pressure-sensitive adhesive layer for attachment to coarse materials.

* * * * *

UNITED STATES PATENT AND TRADEMARK OFFICE
CERTIFICATE OF CORRECTION

PATENT NO. : 4,959,265

DATED : September 25, 1990

INVENTOR(S) : Leigh E. Wood and Allen L. Noreen

It is certified that error appears in the above-identified patent and that said Letters Patent is hereby corrected as shown below:

In Col. 4, line 26, delete the letter "o" and insert therefor --of--.

Signed and Sealed this

Twenty-eighth Day of April, 1992

Attest:

HARRY F. MANBECK, JR.

*Attesting Officer*      *Commissioner of Patents and Trademarks*